United States Patent [19]
Diamond

[11] 4,455,137
[45] Jun. 19, 1984

[54] DENTAL INSTRUMENT AND METHOD FOR POSITIONING A LINGUAL ORTHODONTIC BRACKET

[76] Inventor: Michael K. Diamond, 86 Milburn La., Roslyn, N.Y. 11577

[21] Appl. No.: 424,514

[22] Filed: Sep. 27, 1982

Related U.S. Application Data

[63] Continuation-in-part of Ser. No. 322,193, Nov. 17, 1981.

[51] Int. Cl.³ .............................................. A61C 7/00
[52] U.S. Cl. ...................................................... 433/3
[58] Field of Search ............................................ 433/3

[56] References Cited

U.S. PATENT DOCUMENTS 1,531,898  3/1925  Angle et al. ............................ 433/3
3,330,038  7/1967  Berman .................................. 433/3

Primary Examiner—Robert Peshock

[57] ABSTRACT

A dental instrument and method for positioning a lingual orthodontic bracket is disclosed. The instrument comprises a housing on which is positioned a first arm that includes means for releasably holding the orthodontic bracket. A second arm, which cooperates with the first arm, also cooperates with the housing in such a manner that the spacing between the buccal surface of the tooth and the base of the slot in the bracket that is used for the support thereof may be rapidly determined. Level indicating means are used for displaying the extent of inclination of the first arm with respect to a predetermined plane. Means are also provided for angularly orienting the slot by which the bracket is supported with respect to a predetermined plane. Also described is the combination and cooperation of a novel lingual orthodontic bracket and a novel orthodontic instrument for use with the bracket.

11 Claims, 22 Drawing Figures

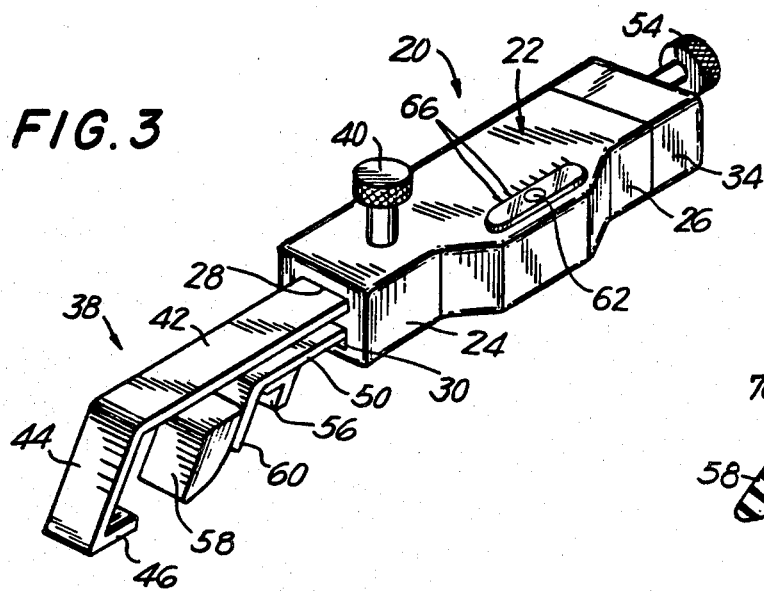
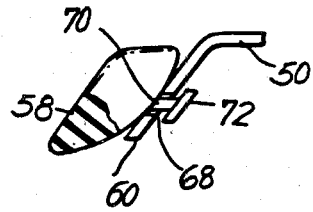
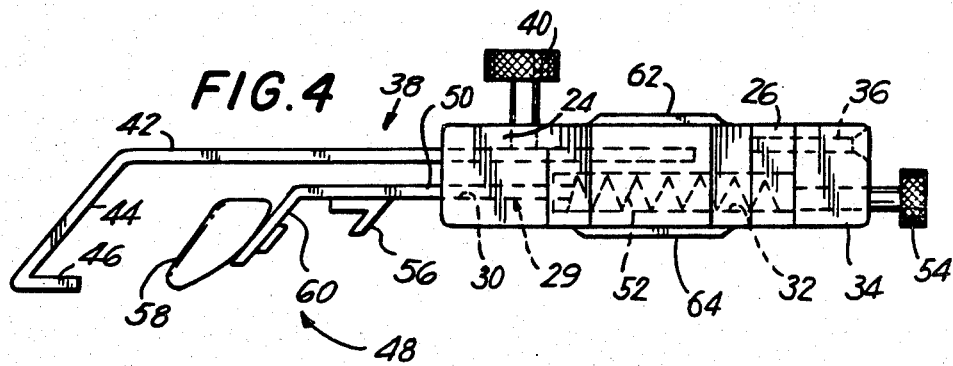
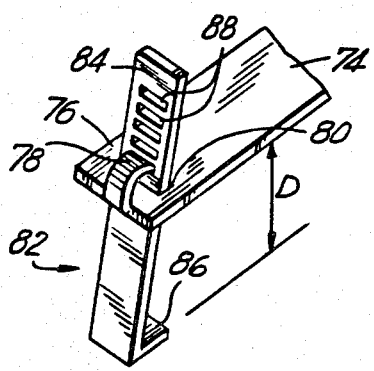
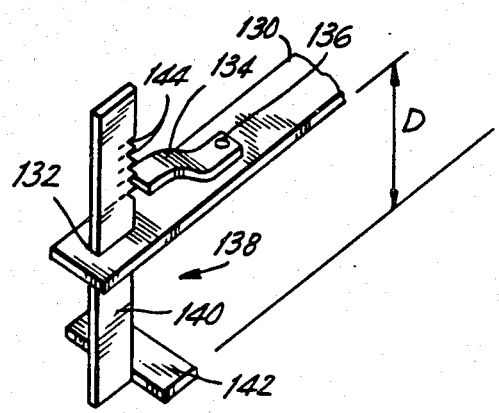

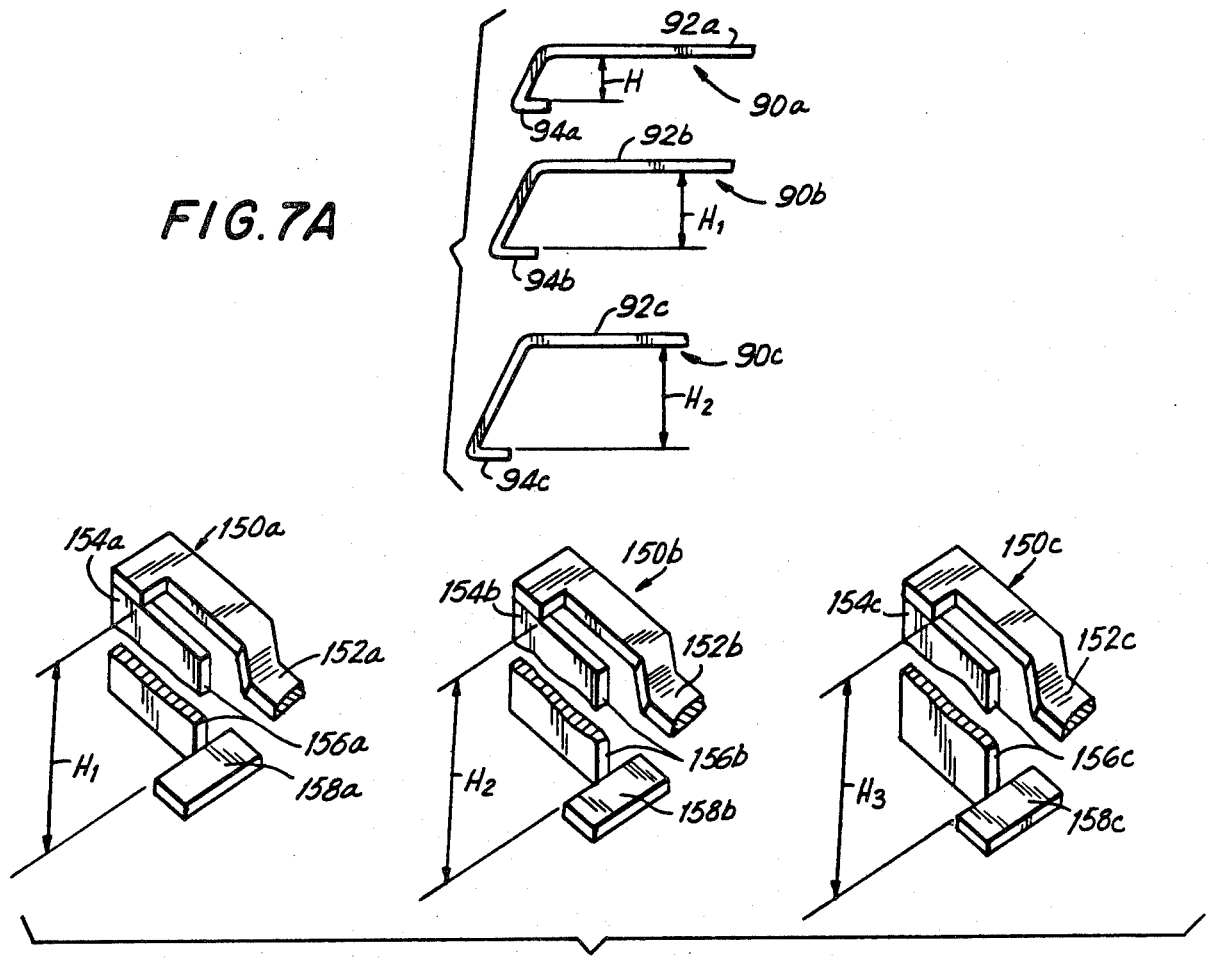
FIG.7A
FIG.7B
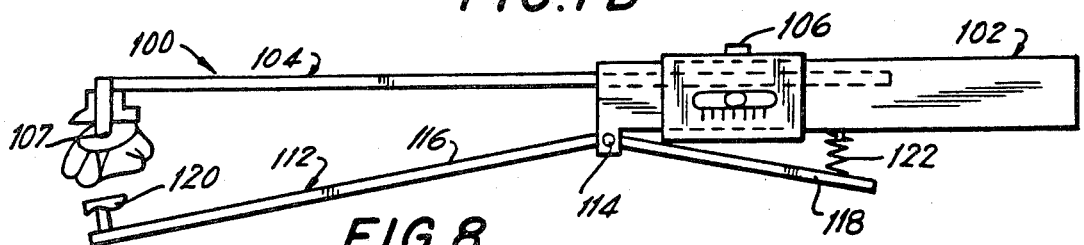
FIG.8
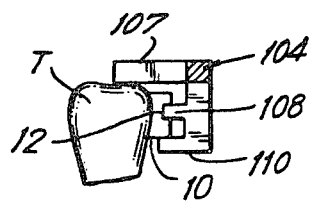
FIG.9A
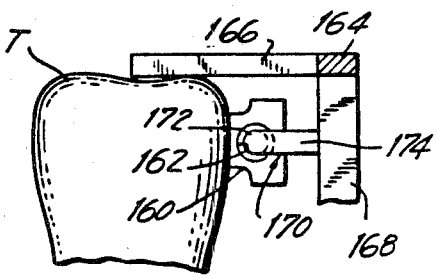
FIG.9B

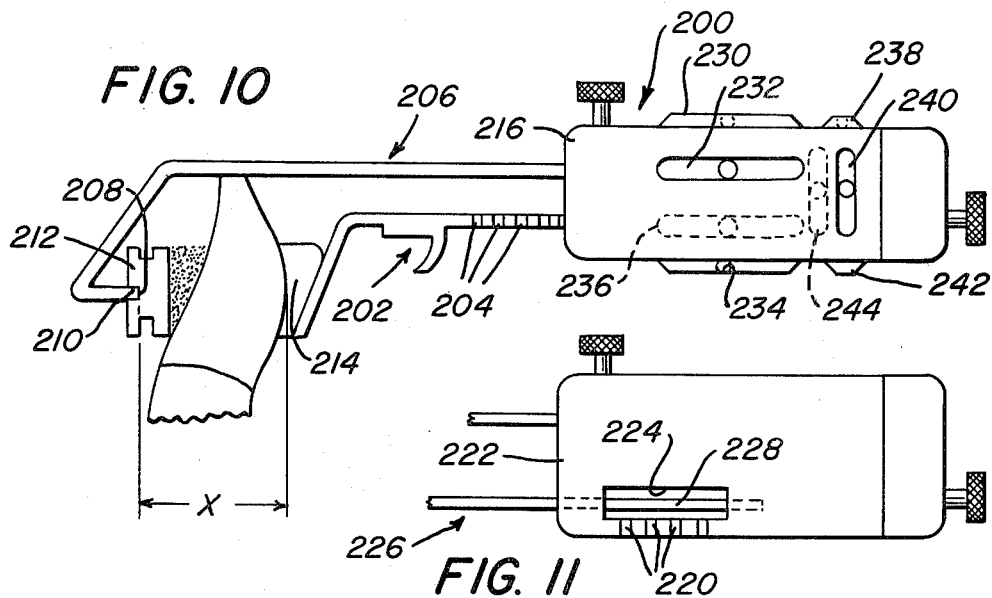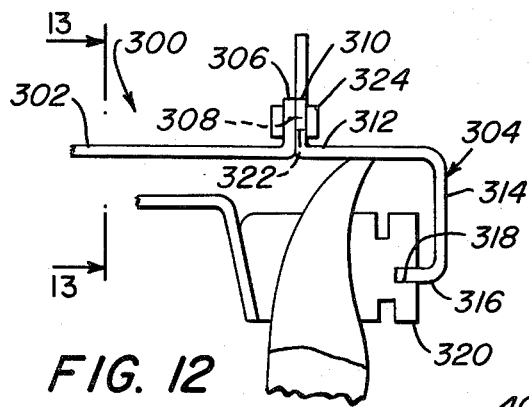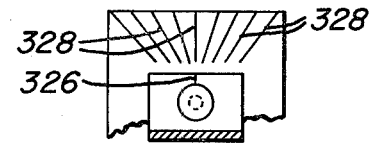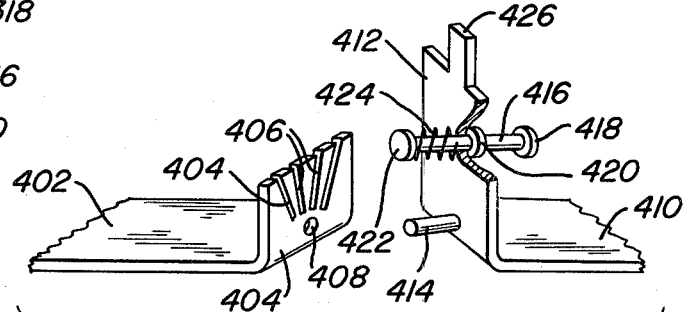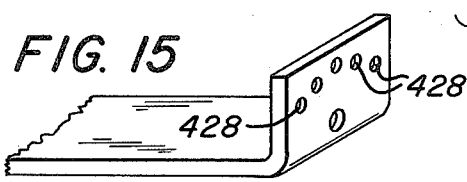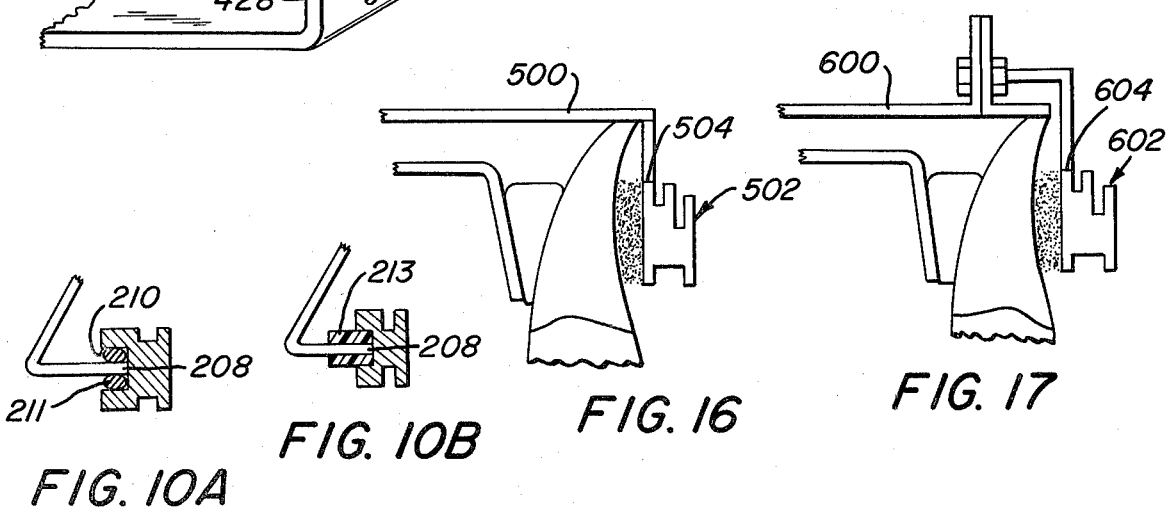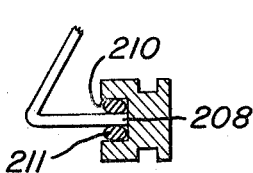

DENTAL INSTRUMENT AND METHOD FOR POSITIONING A LINGUAL ORTHODONTIC BRACKET

This application is a continuation-in-part of my copending application, Ser. No. 322,193 filed Nov. 17, 1981, the contents of which are incorporated herein by reference.

The present invention relates generally to dental instruments and more particularly to an improved instrument and method utilizing the improved instrument for positioning a lingual, orthodontic bracket.

The method most commonly used today for orthodontic treatment involves the correction of malocclusions by attaching metal or plastic brackets to the facial surfaces of teeth. A U-shaped wire is then fitted into these brackets and the position of the misaligned teeth is corrected by sliding the teeth along the wire, using either a pushing or a pulling force. More specifically, and in this prior art method, individual brackets or metal bands with brackets attached to them are secured such as by the use of cement to the facial surface of each tooth. The brackets each have a horizontal and/or vertical slot that is perpendicular and/or parallel, respectively, to the longitudinal axis of the tooth with the slot, when it is horizontal, being at a set distance from the incisal edge or cusp tip of the tooth. An arch wire is positioned in the slots and is secured to the brackets by means of ligatures or pins.

The primary disadvantage of this conventional method is that the brackets and the wires are visible when the mouth is opened because the appliance is attached to the outer surface of the teeth. It will be evident that the profession of many people, particularly adults, precludes the possibility of wearing orthodontic braces of this type. Such group of people would include actors, actresses, business executives, sales people, athletes, etc.

Another prior art form of treating malocclusions utilized metal bands with brackets that were cemented to the molars. A lingually located, heavy arch wire was then attached to the bands and individual ligatures were used to connect the teeth to the arch wire. The ligatures were then periodically tightened. However, because this method of treating malocclusions from the lingual side did not attach each tooth to the arch wire by means of a bracket secured to the tooth, the movements of the teeth were unpredictable and inaccurate. Generally speaking results achieved by this second method were not satisfactory.

The present invention, by way of contrast, utilizes individual brackets, each having a horizontal or vertical slot or both. The brackets are individually cemented to the lingual surface of its respective tooth. If desired or required, orthodontic bands with lingual tubes and buccal or facial attachments are cemented on the molar teeth.

In order to practice the method comprising the present invention, an arch wire is passed into the lingual tubes on the brackets which are mounted on the molars and is engaged in the horizontal or vertical slots of the remaining brackets. The arch wire is held in place by ligatures. If more than one molar is banded, or if a bracket will not adhere to the lingual side of the tooth, a bracket would be placed on the facial side of the tooth and a wire used to connect the bracket on the tooth to the bracket on a molar. Alternatively, two molars could be secured to each other in the same manner. Normally, the molars are utilized as an anchorage and serve to apply a resistance force.

In the event of a deep bite where closure of the mouth causes the teeth to hit the brackets, for example the lower teeth hitting the upper brackets, two different courses of treatment could be used. First of all, only the lower teeth could be treated until the condition is corrected. Alternatively, a removable plastic wafer that covers the occlusal surfaces of the upper or lower teeth could be utilized to prevent the brackets from being traumatized.

The method comprising the present invention contemplates moving the teeth by periodically changing the size of the arch wire or using the same size wire but of a different resiliency or a combination of both. Initially, utilizing the apparatus and method of this invention, each bracket is accurately positioned in space adjacent the lingual surface of the tooth prior to being cemented in place on or close to the vertical center line of the tooth. The dimension or distance of the horizontal or vertical slot in the bracket from the incisal edge or cusp tip varies from tooth to tooth. For example, the brackets placed on the four lower incisors could be at the same level but the bracket placed on the lower canines would be 0.5 mm further from the edge of the tooth. Normally the vertical center line representing the long axis of the tooth's crown is determined either by eye, by calipers or by use of a divider because the precise location is critical. Also, the height or dimension of the bracket slot from the incisal edge or cusp tip of the tooth is critical because ideally, the arch wire engaged in the brackets on the teeth should be in a common plane, thereby enabling the insertion of a standardized straight wire form that would not require bends to adjust for the various ideal tooth positions in a common plane. Also, both the apparatus and method of this invention permit the quick and accurate establishment of the correct angle of the arch wire retaining slot of the lingual bracket.

Prior to the use of the method and apparatus comprising the present invention, accurate placement of the lingual bracket incorporating a horizontal on vertical slot was difficult if not impossible to do directly on a patient's teeth. In order to have accurate and complete control of a tooth's movement, and to position all of the teeth in proper relationship to each other, the bracket slot must be positioned precisely (1) a specific distance from the incisal edge or cusp tip ("Y" axis); (2) on or at a known distance along the long axis of the tooth's crown which is normally the vertical center line ("X" axis); and (3) at a specific distance from the facial or buccal surface of the tooth with a known relationship of the walls of the bracket slot and the long axis of the crown ("Z" axis). It should be kept in mind that time is an additional factor which must be considered. Because the adhesive utilized in cementing brackets used in an orthodontic practice sets relatively fast, the brackets must not only be accurately placed but must also be placed rather quickly.

To the best of my knowledge no instrument presently exists that accurately positions a lingual bracket in the mouth of the patient on or parallel to the vertical center line or long axis of the tooth crown of a tooth at a predetermined distance from the incisal edge or cusp tip of the tooth.

Nor does any dental instrument, to the best of my knowledge, provide means for quickly and accurately determine the space between and position the three walls of a slot in a lingual bracket with respect to the buccal or facial surface of a tooth and long axis of the tooth crown.

The present invention provides an instrument for accurately positioning a lingual orthodontic bracket, for example, on a tooth in the mouth of a patient and includes a housing from which an arm extends. Retaining means are formed integrally with the arm for the purpose of releasably holding an orthodontic bracket utilizing either a vertical or a horizontal slot therein. Further, the retaining means in one embodiment of this invention may be releasably applied to a lingual tube formed on an orthodontic bracket.

When a portion of the arm of the instrument comprising this invention rests on the top surface of the tooth, a level indicating or angle measuring device will display the extent of inclination of the arm with respect to a predetermined plane, for example the horizontal plane. There may be four of these indicating devices, each of which would be mounted on a different surface, with the surfaces being defined by two pair of parallel surfaces with one pair being perpendicular to the other pair. In addition there may also be two indicating devices on each surface with the indicating devices, if they are bubble levels or the like, being perpendicular to each other on any given surface.

The instrument comprising the present invention provides means for adjusting at least a portion of the position of the bracket holding arm in a plane that is either substantially parallel, perpendicular or oblique to the predetermined plane. Advantageously, the instrument comprising this invention further includes an adjustably mounted plate that is located in opposition to that end of the arm which is remote from the housing in order to engage the facial surface of the tooth when the bracket is positioned on the lingual surface of the tooth.

In one embodiment of the present invention the means for displaying the extent of inclination of the arm with respect to the predetermined plane is in the form of a bubble level means mounted in the housing and on which indicia are provided adjacent the bubble level means. In order to permit usage of the present invention with both upper and lower teeth, the level indicating means should at least be on both upper and lower surfaces of the housing.

A particular embodiment of this invention provides means for indicating the location of the bracket retaining arm relative to the housing for the purpose of establishing accurately the dimension between the walls or base of the arch wire slot and the buccal surface of the tooth. Still another embodiment of the apparatus provides means for selectively rotating at least a portion of the bracket supporting arm whereby the orientation of the arch wire slot may be quickly and accurately established at a specific angle, parallel or perpendicular to the long axis of the tooth crown.

Accordingly, it is an object of the present invention to provide an improved orthodontic instrument.

Another important object of the present invention is to provide an improved instrument as described above, for positioning an orthodontic bracket on a tooth.

Still another object of the present invention is to provide an improved instrument, as described above, for positioning a lingual orthodontic bracket on a tooth.

An additional object of the present invention is to provide an improved dental instrument, as described above for positioning a lingual orthodontic bracket on a tooth in the mouth of a patient.

A further object of the present invention is to provide an improved orthodontic instrument, as described above, including means for displaying the extent of inclination of a portion of the instrument with respect to the predetermined plane.

It is another object of the present invention to provide an improved orthodontic instrument, as described above, including means for releasably holding the orthodontic bracket prior to the placement thereof on the lingual surface of the tooth.

An additional object of the present invention, is to provide an improved orthodontic instrument, as described above, including means that can adjustably position a lingual orthodontic bracket either in a plane substantially parallel, perpendicular or oblique with respect to the longitudinal axis of the tooth crown.

Yet another object of the present invention is to provide an improved orthodontic instrument, as described above, that further includes an adjustable plate in spaced opposition to that portion of the instrument that releasably supports the orthodontic bracket with the plate being adapted to engage the facial surface of the tooth when the bracket is positioned relative to the lingual surface of the tooth crown or the long axis of the tooth crown.

A specific object of the present invention is to provide an improved orthodontic instrument, as described above, wherein the level indicating means comprises angle measuring means or a bubble level on at least one surface of the instrument and preferably comprises two bubble levels on surfaces of the instrument that are 180° apart but parallel to each other so that the instrument may be used on both the upper and lower sets of teeth.

It is another object of the present invention to provide an improved orthodontic instrument, as described above, wherein there is included a plurality of means for releasably holding the orthodontic bracket, the plurality or means having a range of dimensions defining a set of means for holding the orthodontic bracket.

An important object of the present invention is to provide an improved orthodontic instrument, as described above, wherein the level indicating means for displaying the extent of inclination of a portion of the instrument with respect to an orthodontic bracket and a predetermined plane includes means responsive to rotation of the instrument about a plane that is substantially parallel to the vertical axis of the tooth crown or long axis of the tooth crown.

Another important object of the present invention is to provide an improved orthodontic instrument, as described above, that is adapted to releasably support a lingual orthodontic bracket utilizing the horizontal slot thereof.

An additional object of the present invention is to provide an improved orthodontic instrument, as described above, that is adapted to support a lingual orthodontic bracket utilizing the vertical slot thereof.

Yet another object of the present invention is to provide an improved orthodontic instrument, as described above, that is adapted to releasably support a lingual bracket that includes a tube for receiving a lingual arch wire, the instrument including a pin that is arranged to be inserted into the lingually located tube on the bracket.

A further object of the present invention is to provide an improved orthodontic instrument, as described above, including means for indicating the distance between the walls or base of the arch wire slot of a lingual bracket and the facial surface of the tooth or long axis of the tooth crown.

Yet another object of the present invention is to provide an improved orthodontic instrument, as described above, including means for selectively orienting the arch wire slot of a lingual bracket with respect to a predetermined reference plane.

These and other objects, features and advantages of the invention will, in part, be pointed out with particularity, and will, in part, become obvious from the following more detailed description of the invention, taken in conjunction with the accompanying drawing, which forms an integral part thereof.

In the drawings, like reference characters designate like parts. In the drawings:

FIG. 3 is a schematic, perspective view illustrating one embodiment of the improved orthodontic instrument comprising the present invention;

FIG. 4 is a side elevational view of the instrument shown in FIG. 3;

FIG. 5 is a fragmentary side elevational view, partially in section, illustrating a feature of the instrument shown in FIG. 3;

FIG. 6A is a fragmentary, perspective view of a modified portion of the instrument shown in FIG. 3 illustrating another feature of the present invention;

FIG. 6B is a fragmentary, perspective view of a portion of an alternative embodiment of the structure shown in FIG. 6A;

FIG. 7A is a schematic illustration of a portion of the instrument shown in FIG. 3 illustrating the applicability thereof as a set of instruments having a range of dimensions;

FIG. 7B is a schematic illustration of a portion of the instrument shown in FIG. 6B showing the applicability thereof as a set of instruments having a range of dimensions;

FIG. 8 is a schematic plan view illustrating an alternative embodiment of the improved orthodontic instrument comprising the present invention;

FIG. 9A is a transverse elevational view, partially in section, taken along 9—9 of FIG. 8;

FIG. 9B is a fragmentary elevational view, partially in section, illustrating an alternative embodiment of the structure shown in FIG. 9A;

FIG. 10 is a side elevational view of another, improved orthodontic instrument comprising the present invention;

FIG. 10A is an enlarged, fragmentary view of a portion of the instrument shown in FIG. 10 illustrating a modification thereof;

FIG. 10B is a view similar to FIG. 10A illustrating a variation of the structure shown therein;

FIG. 11 is a fragmentary side elevational view illustrating a modification of the embodiment shown in FIG. 10;

FIG. 12 is a fragmentary, schematic side elevational view illustrating still another embodiment of the present invention;

FIG. 13 is a transverse sectional elevational view taken along line 13—13 of FIG. 12;

FIG. 14 is an exploded, perspective view schematically and fragmentarily illustrating another form of the improved orthodontic instrument comprising the present invention;

FIG. 15 is a view similar to FIG. 14 illustrating a modification of the embodiment shown therein;

FIG. 16 is a side elevational view illustrating still another embodiment of the present invention; and FIG. 17 is a view similar to FIG. 16 and FIG. 12 illustrating a modification of the embodiments shown therein.

Figure 1:
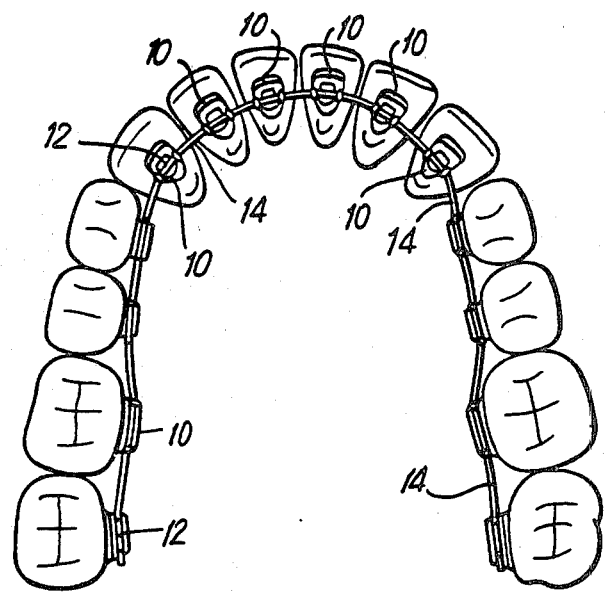
FIG. 1 is a plan view of the mandibular arch illustrating a plurality of lingual, orthodontic brackets adhesively secured to the teeth together with an arch wire held in place my means of ligatures.
Figure 2:
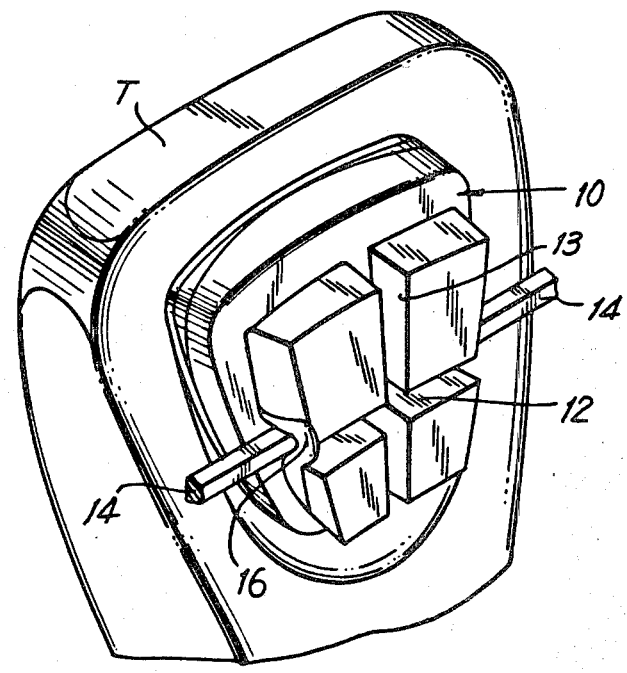
FIG. 2 is an enlarged perspective view of a typical orthodontic bracket used in FIG. 1.

Referring first to FIGS. 1 and 2, there is shown therein a plurality of orthodontic brackets each designated by the reference character 10 and which are each adhesively secured to the lingual surface of the mandibular arch but which, per se, do not form part of the present invention. While there are many different types of brackets 10, each of which has its own special function depending upon the tooth T to which it is applied, the single feature common to all of the brackets 10 which is of importance to the present invention is the transverse and/or vertical slots 12, 13, respectively, shown best in FIG. 2. In a manner well known in the art, an arch wire 14 is positioned in the slots 12, for example, and is resiliently and removably secured to the brackets 10 by means of elastic liguatures 16.

One embodiment of the instrument comprising the present invention is shown in FIGS. 3 and 4 and is designated generally by the reference character 20. The instrument 20 comprises a housing 22 having forward and rearward ends 24 and 26, respectively. A first, slot-like opening 28 is formed in the forward end 24 of the housing 22 and a second, two-part opening 29 comprising coaxial sections 30 and 32 is formed through the rearward end 26 of the housing 22. A closure member 34 is secured to the rearward end 26 of the housing 22 by means of fasteners 36 as shown in FIG. 2.

A primary arm, generally designated by the reference character 38, is slidably received within the first opening 28 and is adapted to be adjustably secured to the housing 22 by means of a set screw or other suitable fastener 40. The primary arm 38 is comprised of a first section 42 that is adjustably positioned in the slot 28, a second section 44 that is integral with and extends from the end of the first section 42 that is remote from the housing 22 and a third relatively short section 46 which, in the embodiment illustrated in FIG. 3 and in FIG. 4 is in a plane that is generally parallel to the plane of the first section 42. In a manner to be described more fully hereinafter, the third section 46 is adapted to releasably engage the transverse slot 12 formed in the bracket 10.

A secondary arm generally designated by the reference character 48 is also slidably and adjustably mounted in the housing 22. The secondary arm 48 comprises a first portion 50 that is adapted to be slidably received in the correspondingly sized and shaped section 30 of the opening 28. However, for purposes to be described more fully hereinafter, the section 30 is somewhat larger than the portion 50 of the secondary arm 48 in order to allow universal movement thereof. A helical compression spring 52 is positioned within the second section 32 in the housing and bears against the rearward end of the secondary arm 48 that extends through the section 30 of the opening 29 in the housing 22. The spring 52 exerts a forwardly directed force against the rearwardly facing end of the secondary arm 48 in order to urge the secondary arm 48 in the direction of the sections 44 and 46 of the primary arm 48. The spring force is controlled by a fastener 54 that is threaded through the closure member 34 and which bears against the rear end of the spring 52.

For purposes of convenience, a trigger 56 is provided on the underside of the secondary arm 48 in order to permit the orthodontist to retract or move the secondary arm 48 rearwardly in a direction away from the sections 44 and 46 of the primary arm 38. Finally, a universally movable labial plate 58 which will be described more fully hereinafter is also provided on the forward end 60 of the arm 48 that is remote from the housing 22.

As shown in FIGS. 3 and 4, bubble levels 62 and 64 are provided on the upper and lower surface of the housing 22 intermediate the ends 24 and 26 thereof. Adjacent each of the bubble levels 62 and 64 are indicia 66 which will indicate the extent of inclination of the primary arm 38 with respect to a horizontal plane when the orthodontist applies the bracket 10 to the tooth T.

An important feature of the present invention is illustrated in FIG. 5. As mentioned hereinabove, it is desirable that the labial plate 58 be universally coupled to the secondary arm 48 so that, when in use, the plate 58 can accommodate itself to the many different inclinations and variations in tooth surfaces. One construction which permits universal play of the plate 58 relies on the slot section 30 being oversized with respect to the same dimensions of the portions 50 of the secondary arm 48. Another form of construction which is illustrated in FIG. 5, relies on the inherent resiliency of the plate 58 which may be made of a soft material such as rubber or the like. Alternatively, the rearward surface of the plate 58 may be provided with a stem 68 that extends through an oversized opening 70 formed in the end portion 60 of the secondary arm 48. In order to retain the plate 58, the stem 68 is provided with a head 72. It will be appreciated that any of the aforementioned forms of construction will provide some degree of universal movement to the plate 58. In this connection it should be noted that a great deal of movement is not required.

Turning now to FIG. 6 there is shown another important feature of the invention. Whereas in the first embodiment of the invention shown in FIG. 3 and FIG. 4 the primary arm 38 was of unitary construction, the alternative embodiment illustrated in FIG. 6A provides for some degree of adjustment of the portion of the primary arm that engages the transverse slot 12 in the bracket 10. In this alternative embodiment, the primary arm 74 is provided at its forward end 76 with a tab 78 and a slot 80. An L-shaped member 82, comprising legs 84 and 86 which are functionally equivalent to the sections 44 and 46, respectively, of the first embodiment of the primary arm 38 shown in FIGS. 3 and 4 is adjustably coupled to the forward end of the primary arm 74. That is, the leg 84 extends through the slot 80 and is releasably and adjustably secured thereto by means of the tab 78 which engages anyone of a plurality of slots 88 formed in the section 84. Thus it will be appreciated that the dimension D between the opposed surfaces of the sections 74 and 86 may be easily varied. This dimension D corresponds to the dimension between the slot 12 in the bracket 10 and the incisor ledge or cusp tip of the tooth T. As mentioned hereinabove, it is this dimension that is most critical in the accurate placement of the bracket 10.

Another alternative embodiment for selectively and securely placing the orthodontic bracket 10 on the lingual surface tooth T is shown in FIG. 7A. This embodiment comprises a plurality of primary arms 90 which define a set of arms 90a, 90b, 90c, etc. Each arm 90 has a different dimension H between sections 92 and 94 thereof. Since it is the section 92a that rests on the incisal edge or cusp tip of the tooth T and the section 94a that engages the transverse slot 12 in each bracket 10, it will be appreciated that, by selectively placing the desired one of the arms 90 in the instrument 20, utilizing the set screw 40 to establish the axial relationship between the selected arm 90 and the housing 22 of the instrument 20, the bracket 10 may be placed at different heights on the vertical center line of the tooth T.

An alternative embodiment of the present invention is illustrated in FIG. 8. The first embodiment described hereinabove is particularly useful when the longitudinal axis of the instrument 20 can assume a position that is substantially perpendicular to the lingual mounting surface of the tooth. However, in those instances where this is not feasible, for example when there is limited space for the application of a bracket 10 on one of the molars, the embodiment illustrated in FIG. 8 can be utilized. This second embodiment contemplates the positioning of the longitudinal axis of the instrument in a plane that is substantially parallel to the lingual mounting surface of the tooth T.

The alternative instrument, generally designated by the reference character 100, comprises a housing 102 having a primary arm 104 that is adjustably positioned thereon by means of a fastener 106 in much the same manner as described in connection with the first embodiment. The primary arm 104, at the end thereof that is remote from the housing 102, includes a transverse extension 107, that is adapted to contact the incisal edge or cusp tip of the tooth T that is to be treated. There is further provided a lip 108 that is adapted to releasably engage the transverse slot 12 in the bracket 10 in the same manner as described in connection with the first embodiment. If desired, a rib 110 as shown in FIG. 9A may be formed on the end of the primary arm 104 that is in opposition to the lip 108 for the purpose of supporting the bracket 10 on the underside thereof.

A secondary arm 112 is mounted intermediate the ends thereof on the housing 102, by means of a pivot pin 114 as shown in FIG. 8. The secondary arm 112 is comprised of first and second sections 116 and 118, respectively, the planes of which define an obtuse angle. The first section 116 of the secondary arm 112 is arranged to support a universally mounted labial plate 120 in much the same manner as described in connection with the first embodiment. The second section 118 of the secondary arm 112 is provided with a compression spring 122 which normally biases the plate 120 in a direction towards the facial surface of the tooth. By deflecting the second section 118 of the secondary arm 112 and thereby compressing the spring 122, the plate 120 will be displaced from the facial surface of the tooth T.

Also mounted on the housing 102 is a sleeve 124, on which is positioned a bubble level 126. It will be seen in FIG. 8 that the longitudinal axis of the bubble level 126 is substantially parallel to the longitudinal axis of the primary arm 104 and therefore substantially perpendicular to the longitudinal axis of the extension 107. Thus by manipulating the instrument 100 about a generally horizontal axis that is substantially perpendicular to the longitudinal axis of the bubble level 126, the relationship of the slot 12 in the bracket 10 can be determined with respect to the predetermined plane, such as the horizontal plane for example. This relationship is of subtantial importance because it is well known that the slot 12 in the bracket 10 should be parallel to the biting surface of the molars.

At this time it should be particularly noted, although it is not specifically illustrated, that each of the instruments 20 and 100, described hereinabove, could have two mutually perpendicular bubble levels on each of the surfaces thereof wherein only one has been described hereinbefore. While somewhat greater skill would be required in manipulating the instruments and reading the bubble levels, it will be appreciated that even more accurate placement of the bracket can be achieved since accurate determination of two mutually perpendicular planes can be read directly. Accordingly, it is intended that the scope of the present invention include two mutually perpendicular bubble levels in two common, parallel planes.

At this time, three modifications of structure hereinbefore discussed will be referred to in connection with FIGS. 6B, 7B and 9B. Referring first to FIG. 6B there is shown therein a modification of the structure illustrated in FIG. 6A. Whereas the leg 86 of the L-shaped member 82 in FIG. 6A is adapted to engage the horizontal slot 12 in the bracket 10, the structure shown in FIG. 6B is adapted to utilize the vertical slot 13 in the bracket 10. The outer end of a primary arm 130 is provided with an opening 132 therethrough as well as leaf spring 134 that is secured in place by means of fastener such as a rivet 136 or the like. An L-shaped member 138 is provided with a first leg 140 which is arranged to extend through the opening 132. The thickness of the leg 140 is approximately the same as or slightly less than the width of the slot 13 and is arranged to be received therein. The leg 140 may serve as means for visually aligning the bracket 10 parallel to or on the longitudinal axis of the tooth crown. At the lower end of the leg 140 there is another leg 142 which serves to support the lower edge of the bracket 10 when the leg 140 is positioned in the slot 13. It will be appreciated that by raising or lowering the L-shaped member 138 in the opening 132, the dimension D can be varied in much the same manner as that described in connection with the embodiment shown in FIG. 6A. That is, the bracket 10 may be placed at different heights from the incisal edge or cusp tip of the tooth T. To facilitate the displacement of the L-shaped member 138, it is desirable that the portion thereof extending above the primary arm 130 be provided with notches 144 which are adapted to be selectively engaged by the leaf spring 134. In this manner it will be relatively simple matter to repeat critical dimensions. In addition, the portion of the L-shaped member 138 extending above the upper surface of the primary arm 130 also serves as means for visually aligning the bracket 10 parallel to the longitudinal axis of the tooth crown.

In FIG. 7B there is shown in a modification of the set of instruments shown in FIG. 7A. Whereas the set of instruments shown in FIG. 7A utilizes the horizontal slot 12 in the bracket 10 for determining the appropoate dimension H of the bracket 10 from the incisal edge or cusp tip of the tooth T, the set of instruments shown in FIG. 7B utilize the vertical slot 13 in the bracket 10 in order to permit a different dimension H to be selected. Each instrument 150a, 150b, 150c, etc. is comprised of a primary arm 152a, the outer end of which is provided with a downwardly depending leg 154a having a major plane that is perpendicular to the plane of the primary arm 152a. The edges 156a, b and c are adapted to engage the vertical slot 13 in the bracket 10 and extend above the primary arms 152a, b and c thereby serving as means for visually aligning the bracket 10 parallel to or at the longitudinal axis of the tooth crown. A second leg 158a, which is in a plane parallel to and spaced from the plane of the primary arm 152a by a dimension $H_1$ is formed integrally at the lower end of the first leg 154a. From the foregoing it will be evident that by constructing a set of primary arms as hereinbefore described but with variations in the dimension H, a set of instruments will result that will permit the accurate placement of brackets 10 at different dimensions from the incisal edge or cusp tip of the tooth T and accurate location with respect to the longitudinal axis of the tooth crown.

The modification of the present invention shown in FIG. 9B represents the structure that may be used with a bracket 160 having a lingual tube 162 rather than the slots 12 and 13 as shown in the bracket 10. The bracket 160 is used primary on molars. The outer end of a primary arm 164 is provided with a transverse extension 166 in much the same manner as the embodiment shown in FIG. 8. A second arm 168 depends from the underside of the primary arm and is provided with an L-shaped pin 170 comprised of a first leg 172 and a second leg 174. When the transverse extension 166 rests on top of the tooth T the bracket 160 will be properly placed because the dimension between the transverse extension 166 and the second leg 174 of the L-shaped pin 170 is preset. Of course it is within the scope of the present invention, although not specifically illustrated, to provide means for varying the spacing between the second leg 174 of the pin 170 and the underside of the transverse extension 166 for the purpose of being able to place the bracket 160 at different vetical locations on the lingual surface of the tooth. It is also within the scope of the present invention to provide the instrument to which the primary arm 164 is attached with bubble level means as described hereinbefore so as to assure the parallel placement of the axis of the tube 162 with respect to the biting surface of the tooth T or the long axis of the tooth crown.

By utilizing one or more embodiments of the instrument comprising the present invention which is described hereinabove or by using any of the heretofore described modifications thereof, the method comprising the present invention may be practiced. To do so, a bracket is mounted on one portion of the instrument comprising the present invention utilizing either the vertical or the horizontal slot in the bracket. Another portion of the instrument comprising the present invention is then brought into engagement with the incisal edge or cusp tip of the tooth. The instrument is then manipulated while maintaining engagement of the second portion of the instrument with the incisal edge or cusp of the tooth until a desired dimension between the horizontal slot in the bracket and the incisal edge or cusp tip of the tooth is attained. The instrument may be manipulated until the bubble in the level means associated with the instrument assumes a predetermined position. This position indicates that the bracket is in the proper position with respect to the incisal edge or cusp tip of the tooth. Depending upon which embodiment of the invention is utilized, the instrument is manipulated about an axis that is either parallel to or perpendicular to the vertical axis of the tooth crown. Manipulation of one embodiment of the present invention about a horizontal axis will assure that either the horizontal slot or the lingual tube in the bracket is accurately located in a horizontal plane.

Referring now to FIG. 10 there is shown still another embodiment 200 which comprises the present invention. The embodiment illustrated in FIG. 10 is, in all major aspects, substantially the same as the embodiment shown in FIG. 3 and will not be described in detail. However, in the FIG. 10 embodiment, the secondary arm 202 is provided with a series of spaced calibrations 204 which provide means for determining the 'X' dimension which could either be the thickness of the tooth from the lingual to the buccal surface or, as illustrated, the dimension from the base of the bracket slot to the buccal surface of the tooth or from the walls of the bracket slot to the buccal surface of the tooth or from the base of the bracket to the buccal surface of the tooth. As shown in FIG. 10, the primary arm 206 is also provided with an end portion 208 which is adapted to be received in the slot 210 of the bracket 212. When the plate 214 is positioned against the facial surface of the tooth, as illustrated in FIG. 10, then the dimension from the base of the slot 210 of the bracket 212 can very accurately be determined by noting the calibration 204 that is adjacent the housing 216 of the instrument 200. It is a relatively simple matter to assign a specific linear dimension to each of the calibrations 204.

When the desired dimension 'X' is known the instrument can be set with the appropriate calibration 204 adjacent the housing 216. The bracket 212 will then be positioned in space at the desired location. An adhesive material 218 may then be employed intermediate the base surface of the bracket 212 and the opposing lingual surface of the tooth.

In order to aid in the releasable coupling of the end portion 208 and the bracket slot 210, a resilient member such as an O-ring 211 (FIG. 10A) or a plastic sleeve 213 (FIG. 10B) may be employed. Both are readily compressible and will functionally engage the bracket slot. The O-ring 211 may be replaceably retained on the end portion 208 by means, of an annular groove while the sleeve 213 may merely be slipped on and off and retained adhesively on the end 208 if necessary.

FIG. 11 illustrates a modification of the structure shown in FIG. 10. In the FIG. 11 embodiment calibrations 220 are placed in a suitable location on the housing 222 adjacent a window 224 through which a secondary arm 226 may be observed. In contrast to the modification shown in FIG. 10, the FIG. 11 structure provides a single indicating mark 228 on the secondary arm 226. The indicator mark 228 then registers with an appropriate one of the calibrations 220 on the housing 222 so that the 'X' dimension shown in FIG. 10 may be readily determined.

As described hereinabove, all of the foregoing embodiments provide the possibility of an indicating means on each surface. As shown in FIG. 10 the housing 216 is provided with indicating means 230, 232, 234 and 236. Each of these may be a bubble level or angle measuring device. In addition, each of the four, mutually perpendicular surfaces of the housing 216 is provided with a second bubble level or angle measuring device designated by the reference characters 238, 240, 242 and 244, respectively. Each of these second bubble levels is perpendicular in orientation to the bubble level that is on the same surface. Accordingly, manipulation of the instrument in several different, mutually perpendicular planes may be readily observed. It should be understood, although it is not illustrated, that the same arrangement of indicating means applies to the FIG. 11 embodiment as well.

From the foregoing it will be evident that an improved method and instrument for positioning a lingual, orthodontic bracket has been disclosed. The instrument includes means for releasably engaging either the horizontal or vertical slot in the bracket or for engaging a lingual tube prior to adhesively securing the bracket to the lingual surface of the tooth. The various embodiments and modifications of the present invention are particularly applicable to positioning a lingual bracket and provide for attachment on the tooth of a patient. Specifically, the bubble level means or angle measuring devices that are incorporated in the instrument comprising the present invention provides, in combination with suitable indicia on the instrument, effective means suitable for displaying the extent of inclination of a portion of the instrument with respect to a predetermined plane or the long axis of the tooth crown. In this manner the height of the bracket or the distance thereof from the incisal edge or cusp tip of the tooth may be very accurately determined. Thus, this accurate placement may be repeated from tooth to tooth as required. The bubble level or angle measuring devices also enable the instrument to display the extent of inclination that the slot in the bracket has with the long axis of the tooth crown, the surface of the lingual side of the tooth, the facial surface of the tooth and a predetermined plane or position of the slots in brackets on other or adjacent teeth. In addition the instrument provides for accurate measurement of the bracket slot from the incisal edge or cusp tip. Further, the instrument provides for the accurate alignment of the bracket holding arm parallel to or at the longitudinal axis of the tooth crown which would represent the vertical mid-line. In this manner the slot of the bracket can be positioned in space relative to the tooth crown in three measurable planes thereby enabling the location of a point in space on the three axes of height, width and depth. A further embodiment enables the instrument to transfer this point location into a plane surface base or wall of the bracket slot and place it at a known inclination to the longitudinal axis of the tooth crown and to relate the position of the base or walls of the bracket slots to all of the teeth on which the brackets are being placed.

FIGS. 12-15 illustrate still another aspect of the present invention. In one embodiment, as shown particularly in FIGS. 12 and 13, means are provided for accurately orienting the arch wire slot in the bracket. For purposes of this discussion it should be particularly noted that the structural distinction of the FIGS. 12 and 13 embodiment reside completely in the primary arm. Accordingly, an explanation of the structure of the remaining portion of the instrument, which may be of the type shown in FIGS. 4 or 10, will not be made at this time.

The embodiments shown in FIGS. 12 and 13 comprise a primary arm 300 which is formed by inner and other sections 302 and 304. The left hand end of the inner section 302, which is not shown in FIG. 12, is slidably received in a housing similar to that shown in FIGS. 3 and 10. The opposite, or right hand end, of the inner section 302 is provided with an upwardly extending leg 306 in which is formed an axial bore 308.

The outer section 304 is comprised of an upstanding leg 310 which overlays the leg 306 in the first section 302, a portion 312 which is intended to engage the incisal edge of the tooth in the manner described hereinbefore, a downwardly extending section 314 and a lip 316 which engages the slot 318 of the bracket 320. A bore 322 is provided in the leg 310 in coaxial relationship with the bore 308 in the upstanding leg 306 in order to receive a pivot pin 324.

As shown particularly in FIG. 13, there is a single marker 326 formed on the upstanding leg 306 and a plurality of angularly oriented indicia 328 formed on the upstanding leg 310. It will be appreciated then that as the outer section 304 is angularly displaced about the pivot pin 324 the angular orientation of the lip 316 thereof and the slot 318 of the bracket 320 will be similarly displaced. Because of the juxtaposition of the indicia 326 and 328 on the upstanding legs 306 and 310, respectively, the angular orientation of the slot 318 may be readily determined. It is intended that the outer section 304 be pivotly coupled to the inner section 302 by any simple means such as a friction fit of the pivot pin 324 with the opening 308 and 322 through which it extends. Of course other arrangements may be employed. In any event, the embodiments shown in FIGS. 12 and 13 provide for infinitely variable orientation of the bracket slot.

While the lip 316 shown in FIG. 12 is situated in a generally horizontal plane so that the slot 318 in the bracket 320 may be oriented thereabout, it should be understood that means such as shown in FIGS. 7A and 7B may also be utilized for engaging a vertical slot in a bracket for the purpose of altering the orientation of the bracket about a vertical axis.

Although the embodiment of FIG. 12 provides for infinitely variable orientation of the outer section of the primary arm, the embodiment shown in FIG. 14 provides for incrementally variable orientation. In order to accomplish this, the inner section 402 in the embodiment shown in FIG. 14 is provided with an upstanding leg 404 on which is formed a plurality of angularly oriented slots 406 as well as an axial opening 408. Similarly, the outer section 410 is provided with an upstanding leg 412 which includes a pivot pin 414 that is adapted to mate with the opening 408 in the upstanding leg 404 of the inner section 402. A locking pin 416 is also formed in the upstanding leg 412 and is provided with a head 418 and two axially spaced apart shoulders 420 and 422. A compression spring is positioned about the pin 416 intermediate the shoulder 422 and the upstanding leg 412. The portion of the pin 416 intermediate the shoulder 420 and the spring 424 is adapted to be received in a selected one of the slots 406. The spring 424 biases the two legs 406 and 412 into engagement with each other. When the pin 416 is retracted and the spring 424 is compressed and the pivot pin 414 is concurrently pulled out of the opening 408. In this manner the outer section 410 may be angularly oriented with respect to the inner section 402 by manipulating a lever 426 that is provided for this purpose.

In the modification of the last described embodiment as shown in FIG. 14, whereas the slots 406 were formed in the inner section 402, the modification shown in FIG. 15 contemplates the use of a plurality of openings 428 arranged in an arcuate form in order to receive a locking pin similar to the one designated by the reference character 416 in the FIG. 14 embodiment. It will be appreciated that with the structure in FIG. 14 as well as FIG. 15, incremental variation of the angular orientation of the slot in the bracket can be achieved.

FIGS. 16 and 17 illustrate the manner in which the apparatus comprising the present invention may be advantageously combined with a novel bracket. In FIG. 16, a unitary primary arm 500, of the type shown in FIG. 10, is frangibly coupled to a bracket 520 on the top surface thereof. After the bracket 502 is properly cemented in place it is snapped off at a weakened area 504 and a new arm 500, together with its own bracket is set into the instrument.

The embodiment shown in FIG. 17 is essentially the same as that of FIG. 16 except that it utilizes a two-part primary arm 600 to which a bracket 602 is frangibly connected at a weakened juncture 604.

There have been disclosed heretofore the best embodiments of the invention presently contemplated. However, it is to be understood that various changes and modifications may be made thereto without departing from the spirit of the invention.

What I claim as new and desire to secure by U.S. Letters Patent is:

1. An instrument for positioning a lingual orthodontic bracket, said instrument comprising:
   (a) a housing;
   (b) a first arm extending from said housing and including means for releasably holding the orthodontic bracket;
   (c) a second arm extending from said housing and including an end portion in opposition to said bracket holding means; and
   (d) indicia means for indicating the relative position of a portion of said second arm with respect to a portion of said housing whereby the distance between said bracket holding means and said end portion of said second arm may be determined.

2. The instrument according to claim 1 wherein said indicia means are comprised of a plurality of equally spaced apart marks formed on said second arm adjacent the portion of said housing from which said second arm extends.

3. The instrument according to claim 1 wherein there is a window in said housing whereby a portion of said second arm is visible therethrough, said indicia means comprising a plurality of cooperating marks on said housing and said second arm.

4. The instrument according to claim 3 wherein there are a plurality of said marks on said housing and a single mark on the portion of said second arm that is visible through said window.

5. The instrument according to claim 1 wherein said first arm is comprised of two coaxial sections and pivot means coupling said sections of each other whereby said section remote from said housing may be angularly displaced with respect to said section more closely adjacent said housing.

6. The instrument according to claim 5 wherein there are a plurality of equally spaced apart marks on one of said sections and a single mark on said other section.

7. The instrument according to claim 6 wherein said plurality of marks are on said section most closely adjacent said housing.

8. The instrument according to claim 5 wherein there are a plurality of equally spaced apart notches on one of said sections and a pin on said other sections with said pin being adapted to engage a selected one of said notches.

9. The instrument according to claim 8 wherein said notches are on said section most closely adjacent said housing.

10. The instrument according to claim 5 wherein there are a plurality of equally spaced apart holes through one of said sections and a pin in said other section with said pin being adapted to engage a selected one of said holes.

11. The instrument according to claim 10 wherein said holes are in said section most closely adjacent to said housing.

* * * * *